United States Patent [19]

Harnisch et al.

[11] Patent Number: 5,013,627
[45] Date of Patent: May 7, 1991

[54] ELECTROPHOTOGRAPHIC TONERS WITH CATIONIC CHARGE INCREASING ADDITIVE

[75] Inventors: Horst Harnisch, Much; Roderich Raue, Leverkusen, both of Fed. Rep. of Germany

[73] Assignee: Bayer Aktiengesellschaft, Leverkusen, Fed. Rep. of Germany

[21] Appl. No.: 390,557

[22] Filed: Aug. 7, 1989

[30] Foreign Application Priority Data

Aug. 19, 1988 [DE] Fed. Rep. of Germany ....... 3828193

[51] Int. Cl.$^5$ ............................................. G03G 9/097
[52] U.S. Cl. ...................................... 430/110; 546/37; 546/63; 544/124; 544/125; 544/361; 548/431; 548/472; 548/482
[58] Field of Search ......................................... 430/110

[56] References Cited

U.S. PATENT DOCUMENTS

| | | | |
|---|---|---|---|
| 4,493,883 | 1/1985 | Gruber et al. | 430/110 |
| 4,812,379 | 3/1989 | Harnisch et al. | 430/110 |
| 4,841,052 | 6/1989 | Harnisch et al. | 544/361 |
| 4,927,729 | 5/1990 | Harnisch et al. | 430/110 |

FOREIGN PATENT DOCUMENTS 61-156144  7/1986  Japan .................................... 430/110

OTHER PUBLICATIONS

Journal of Heterocyclic Chemistry, R. N. Castle; vol. 15, No. 1, Jan. 1978, pp. 32–37.
Patent Abstracts of Japan, Band 10, No. 188 (P-473) [2244], Jul. 3, 1986, JP-A-6134554.

*Primary Examiner*—Roland Martin
*Attorney, Agent, or Firm*—Sprung Horn Kramer & Woods

[57] ABSTRACT

Positively charged electrophotographic toners contain, besides customary resin and pigment particles, an additive which increases the cationic charge and has the general formula $$(X^1)^- K^{+1} - Y^1 - A - Y^2 - K^{+2} (X_2)^- \qquad (I)$$

wherein the symbols have the meaning mentioned in the description.

8 Claims, No Drawings

ELECTROPHOTOGRAPHIC TONERS WITH CATIONIC CHARGE INCREASING ADDITIVE

The invention relates to positively charged electrophotographic toners which contain, besides customary resin and pigment particles, an additive which increases the cationic charge and has the general formula

   (I)

wherein $(X^1)^-$ and $(X^2)^-$ independently of one another represent an anion, $K^{+1}$ and $K^{+2}$ independently of one another represent

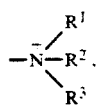

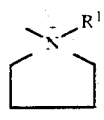 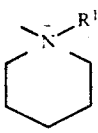 

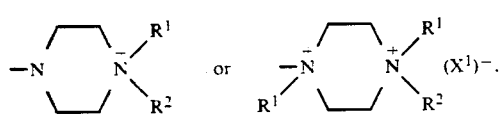

$R^1$ represents $C_1$-$C_{22}$-alkyl, benzyl, phenyl, cyclohexyl or allyl, $R^2$ represents hydrogen or $C_1$-$C_4$-alkyl, $R^3$ represents $C_1$-$C_4$-alkyl and $Y^1$ and $Y^2$ independently of one another represent $C_2$-$C_5$-alkylene or —$C_6H_4$—$CH_2$—* (—m or —p), the bond marked with * being attached to A, and A denotes a tetracarboxylic acid diimide of the formulae

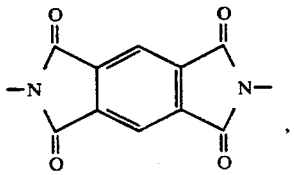

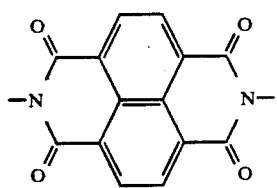

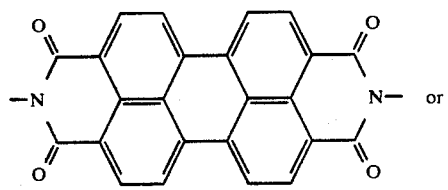

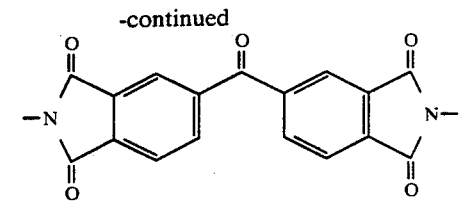

or a 3-amino-1-iminoisoindolenine of the formula:

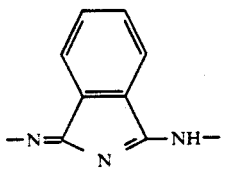

and wherein the cyclic and acyclic radicals can carry customary non-ionic substituents, to the use of the compounds (I) in electrophotographic toners and to new compounds of the general formula $(X^1)-K^{+3}-Y^3-A-Y^4-K^{+4}(X^2)$   (II)

wherein $K^{+3}$ and $K^{+4}$ independently of one another represent

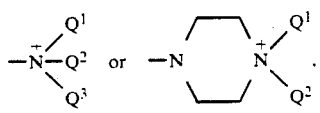

$Q^1$ represents $C_8$-$C_{18}$-alkyl, $Q^2$ represents hydrogen, methyl or ethyl, and $Y^3$ and $Y^4$ independently of one another represent $C_2$-$C_5$-alkylene and $(X^1)^{31}$, $(X^2)^{31}$ and A have the same meaning as in formula (I).

Particularly suitable toners contain symmetrical compounds of the formula (I) wherein $(X^1)^{31}$ is $(X^2)^{31}$, $K^{+1}$ is $K^{+2}$ and $Y^1$ is $Y^2$.

Toners of particular technical value are those containing symmetrical compounds of the formula (II) wherein $(X^1)^-$ is $(X^2)^-$, $K^{+3}$ is $K^{+4}$ and $Y^3$ is $Y^4$.

Examples of suitable non-ionic substituents on cyclic and acyclic radicals are $C_1$-$C_4$-alkyl, halogen, such as chlorine and bromine, hydroxyl, $C_1$-$C_4$-alkoxy, $C_1$-$C_4$-alkoxycarbonyl, carbamoyl or sulphamoyl radicals which can be substituted by 1 to 2 $C_1$-$C_4$-alkyl radicals, or phenyl radicals.

Particularly suitable substituents on alkyl radicals are chlorine, hydroxyl, $C_1$-$C_4$-alkoxy, $C_1$-$C_4$-alkoxycarbonyl and carbamoyl radicals.

Preferred radicals $R^1$ are $C_1$-$C_{22}$-alkyl, carbamoyl-$C_1$-$C_2$-alkyl, $C_1$-$C_4$-alkoxycarbonyl-$C_1$-$C_2$-alkyl, benzyl, cyclohexyl and allyl.

$R^2$ and $R^3$ preferably represent $C_1$-$C_4$-alkyl radicals.

Suitable anions are customary anions, such as halides, for example chloride, bromide and iodide, tetrafluoborates and anions of alkylsulphonic, alkylcarboxylic, alkylphosphoric and alkylphosphonic acids and arylsulphonic, arylcarboxylic, arylphosphoric and arylphosphonic acids. Anions which lower the solubility in water of the compounds (I) are particularly suitable. The reduction in water-solubility can, however, also be effected by enlarging the alkyl radical $R^1$, that is to say choosing a radical within the range of about $C_8$–$C_{22}$-alkyl. In this case more hydrophilic anions, such as halides, are also most suitable.

The preferred water-solubility of the compounds (I) at 20° C. is less than 3% by weight, in particular less than 1% by weight. In addition to halides and tetrafluoborates preferred anions are, in particular, arylsulphonates, such a benzenesulphonates which are optionally substituted by $C_1$–$C_{12}$-alkyl or chlorine, $C_5$–$C_{18}$-alkylsulphonates, salts of $C_5$–$C_{18}$-alkylcarboxylic acids and of condensation products formed from formaldehyde and aryl sulphones and/or optionally sulphonated 4,4'-dihydroxydiphenyl sulphone and anions of heteropolyacids based on tungsten and/or molybdenum together with phosphorus or silicon, in particular phosphotungstomolybdates.

The compounds of the formula (I) can be prepared by methods which are known in themselves, for example in accordance with U.S. Pat. No. 3,544,303, DE-AS (German Published Specification) 3,535,496 and Chem. Abstr. 74 (17), 87 691a, 76 (7), 33 987z, 77 (5), 28 760m and 93, 106 696m by subjecting, for example, tetracarboxylic dianhydrides of the formulae

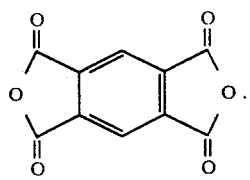

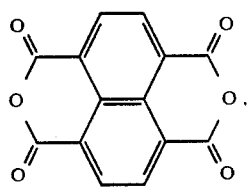

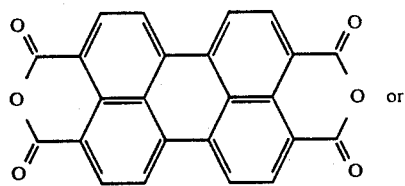

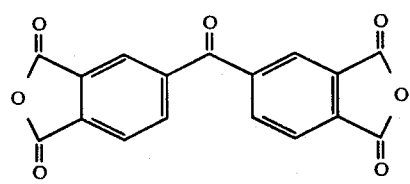

or an isoindolenine of the formula

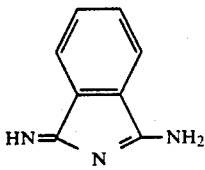

successively or simultaneously to a condensation reaction with in each case one equivalent of an amine of the formulae $$B^1-Y^1-NH_2 \text{ and } B^2-Y^2-NH_2$$

wherein
$Y^1$ and $Y^2$ have the meaning indicated above,
$B^1$ and $B^2$ represent

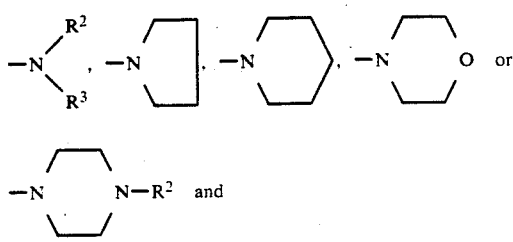

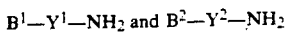

$R^2$ and $R^3$ have the meaning indicated above,
then quaternizing the resulting condensation product successively or at the same time by means of 2 equivalents of $R^1$—X, wherein X represents a radical which can be split off as an anion, and, if appropriate, then changing the anion by known methods, for example analogously to DE-A 3,738,948.

The compounds of the formula (I) are in most cases nearly colourless or are only slightly coloured. Compounds of the formula (I) in which A represents

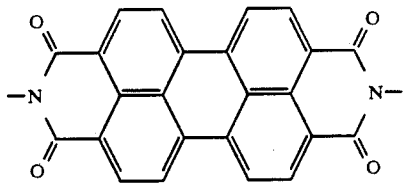

are cationic red dyestuffs.

Additives for electrophotographic toners which increase their charge, also known as charge control substances, are already known. They are described, for example, in DE-A 3,604,827 and 3,738,948, EP-A 233,544, U.S. Pat. Nos. 3,893,935, 3,944,493, 4,007,293, 4,079,014, 4,265,990, 4,298,672, 4,338,390, 4,394,430 and 4,493,883 and JP-A 61-156,144.

Latent electrostatic image recordings are developed by the toner being deposited by induction on the electrostatic image. The charge control substances increase the cationic charge of the toner. This makes the image stronger and of sharper outlines.

The resins present in the toners are known. They are thermoplastic and have a softening point between 50° and 130° C., preferably between 65° and 115° C. Examples of resins of this type embrace polystyrene, copolymers of styrene with an acrylate or methacrylate, copolymers of styrene with butadiene and/or acrylonitrile, polyacrylates and polymethacrylates, copolymers of an acrylate or methacrylate with vinyl chloride or vinyl acetate, polyvinyl chloride, copolymers of vinyl chloride with vinylidene chloride, copolymers of vinyl chloride with vinyl acetate, polyester reins (U.S. Pat. No. 3,590,000), epoxy resins, polyamides and polyurethanes.

In addition to the compounds (I) and the thermoplastic resins, the toners according to the invention contain known amounts of colouring materials and, if appropriate, material capable of magnetic attraction. The colouring material can consist of an organic dyestuff, such as nigrosine, Analine Blue, 2,9-dimethylquinacridone, C. I. Disperse Red 15 (=C. I. 607,710), C. I. Solvent Red 19 (=C. I. 26,050), C. I. Pigment Blue 15 (=C. I. 74,160), C. I. Pigment Blue 22 (=C. I. 69,810) and C. I. Solvent Yellow 16 (=C. I. 12,700), or an inorganic pigment, such as carbon black, red lead, yellow lead dioxide or chrome yellow. In general, the amount of colouring material present in the toner does not exceed about 15% by weight.

The material capable of magnetic attraction can, for example, consist of iron, nickel, chromium oxide, iron oxide or a ferrite of the general formula $MFe_2O_4$ wherein M represents a divalent metal, such as iron, cobalt, zinc, nickel or manganese.

The preparation of the toners containing the compounds (I) is effected by customary processes, for example by mixing the constituents in a kneader followed by pulverizing or by melting the thermoplastic resin or a mixture of thermoplastic resins, followed by fine comminution of one or more charge control substances of the formula (I), and of the other additives, if used, in the molten resin using the mixing and kneading machines known for this purpose, followed by cooling the melt to give a solid mass and finally grinding the solid mass to give particles of the desired particle size. It is also possible to suspend the thermoplastic resin and the compound (I) in a common solvent and to incorporate the other additives into the suspension. The suspension can be used in this way as a liquid toner.

The liquid can, however, also be spray-dried in a manner which is known in itself or the solvents can be removed by evaporation and the solid residue can be ground to give particles of the desired particle size.

In accordance with one modification of this process of preparation, the charge control substance of the formula (I) is not dissolved, but is finely dispersed, in the solution of the thermoplastic resin.

The toner formulation thus obtained is then employed, for example analogously to U.S. Pat. No. 4,265,990, in a xerographic image recording system.

The charge control substances used must meet a variety of requirements.
1. The capacity to develop the latent electrostatic image to give a deeply coloured visible image.
2. Easy dispersibility in the toner formulation and uniform distribution on the surface of the image, in order to produce a trouble-free, uniform image with sharp outlines.
3. Insensitivity to moisture.
4. Good heat stability.
5. Stability to the hot mixture of lead dioxide and a vinylidene fluoride/hexafluoropropylene copolymer resin (for example VITON ®E-430 made by Dupont), by means of which the image can be fixed with the aid of a hot roller. The coating composition must not turn black as the result of decomposition products.

The charge control substances known from the abovementioned patent specifications and published specifications do not meet all these requirements.

It has now been found, surprisingly, that, compared with the hitherto known cationic compounds mentioned, the substances of the formula (I) display a further increase in the depth of colour of the developed image, a further improvement in the sharpness of the image, an even lower sensitivity to high atmospheric humidity and an even higher service life of the toner (more than 70,000 copies).

Example 1

218 g of 1,2,4,5-benzenetetracarboxylic dianhydride (1 mol) are dissolved at 120° C. in 500 ml of N-methylpyrrolidone, and 1 l of o-xylene and 6 g of triethylamine are added and 225 g of N,N-dimethyl-1,3-diaminopropane (2.2 mol) are added dropwise under reflux and under a water separator. A colourless, crystalline precipitate is deposited. The mixture is heated for a further 10 hours under reflux under the water separator, a further 6 g of triethylamine are added and the mixture is heated for a further 6 hours under reflux under the water separator. After this time a total of 36 ml of water has separated out. The reaction mixture is cooled with stirring. The colourless, crystalline precipitate is filtered off with suction, washed with methanol and dried in vacuo at 50° C. This gives first 134 g and, after evaporating the mother liquor and stirring the residue with 500 ml of isopropanol, a further 151 g, that is to say altogether 285 g (74% of theory) of the compound of the formula

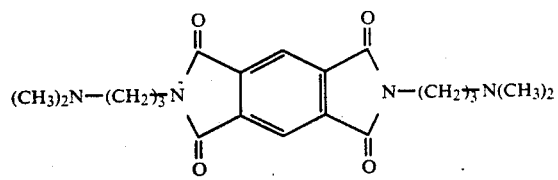

in the form of colourless crystals of melting point 280° to 282° C.

$C_{20}H_{26}N_4O_4$ (386.45), $m/e=386$ (M+).

Example 2

213 g of the compound of Example 1 (0.55 mol) are dissolved in 1.8 l of isopropanol at 80° C. and are heated to the boil under reflux and under $N_2$ with 397 g of 1-bromohexadecane (1.3 mol) for 24 hours, in the course of which the reaction product is deposited in crystalline form even at boiling temperature. After cooling to room temperature the crystalline precipitate is filtered off with suction and is washed with isopropanol and dried in vacuo at 50° C. This gives 526.5 g (96% of theory) of the compound of the formula

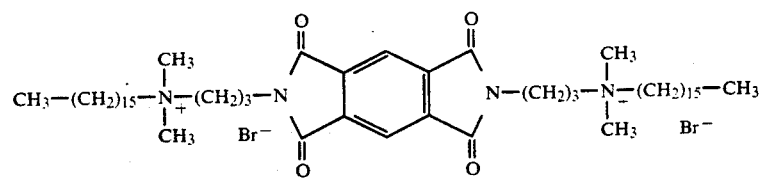

$C_{52}H_{92}Br_2N_4O_4$ (997.14)

According to thin layer chromatography the substance is virtually pure and it exhibits fluorescence extinction on the fluorescent silica gel plate (R$_f$ value: 0.32, mobile phase: 45% by volume of butyl acetate, 33% by volume of glacial acetic acid, 9% by volume of formic acid and 13% by volume of water). It is ground in a jet mill until an average particle size of <10 μ has been reached.

Use

2% by weight of the compound of Example 2, 6% by weight of carbon black and 92% by weight of a styrene/butadiene resin containing 89% by weight of styrene and 11% by weight of butadiene are melted and kneaded in an extruder at 100° C. and are then comminuted and ground until the particle diameter is less than 5 μ.

This toner formulation is incorporated in a xerographic image recording system such as is described in U.S. Pat. No. 4,265,990. This is effected by coating a MYLAR ® substrate with a layer of polyvinylcarbazole which produces a charge when exposed to light and into which trigonal selenium has been freely dispersed, and applying over this a transparent, charge-transporting layer containing as the charge-transporting molecules N,N'-diphenyl-N,N'-bis-(3-methylphenyl)-1,1,'-bisphenyl 4,4'-diamine, dispersed in a MAKROLON ® polycarbonate composition.

This gives image recordings of copperplate sharpness which are also superior in sharpness of outline to those prepared in accordance with U.S. Pat. No. 4,493,883, Example 1.

The following compounds are prepared analogously to Examples 1 and 2:

| Example | K̄ | An⁻ | Y |
|---|---|---|---|
| 3 | CH$_3$—(CH$_2$)$_{17}$—N$^+$(CH$_3$)$_2$— | Br⁻ | —(CH$_2$)$_3$— |
| 4 | CH$_3$—(CH$_2$)$_{21}$—N$^+$(CH$_3$)$_2$— | Br⁻ | —CH$_2$—CH$_2$— |
| 5 | CH$_3$—(CH$_2$)$_{11}$—N$^+$(CH$_3$)$_2$— | CH$_3$—C$_6$H$_4$—SO$_3^-$ | —(CH$_2$)$_3$— |
| 6 | CH$_3$—(CH$_2$)$_9$—N$^+$(CH$_3$)$_2$— | Cl⁻ | —(CH$_2$)$_3$— |
| 7 | CH$_3$—(CH$_2$)$_3$—N$^+$(CH$_3$)$_2$— | I⁻ | —(CH$_2$)$_3$— |
| 8 | H$_2$N—CO—CH$_2$—N$^+$(CH$_3$)$_2$— | Cl⁻ | —(CH$_2$)$_3$— |
| 9 | C$_6$H$_5$—CH$_2$—N$^+$(CH$_3$)$_2$— | Cl⁻ | —(CH$_2$)$_3$— |
| 10 | (CH$_3$)$_3$N$^+$— | CH$_3$SO$_4^-$ | —(CH$_2$)$_3$— |
| 11 | (C$_2$H$_5$)$_3$N$^+$— | C$_2$H$_5$SO$_4^-$ | —(CH$_2$)$_2$— |
| 12 | N-methyl-N-hexadecyl piperazinium (H$_3$C, CH$_3$—(CH$_2$)$_{15}$ on N$^+$) | Br⁻ | —CH$_2$—CH$_2$— |

-continued

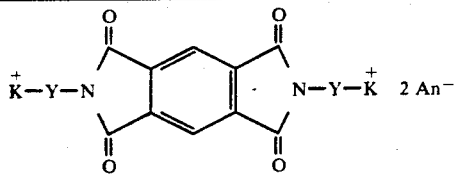

| Example | $\overset{+}{K}$ | $An^-$ | Y |
|---|---|---|---|
| 13 | HOCH₂CH₂–N⁺(CH₃)(piperazine)N– | CH₃–COO⁻ | –CH₂–C(CH₃)₂–CH₂– |
| 14 | cyclohexyl–N⁺(H)(CH₃)(CH₃) | Br⁻ | –(CH₂)₃– |
| 15 | CH₂=CH–CH₂–N⁺(CH₃)₃ | Cl⁻ | –CH₂–(p-C₆H₄)– |
| 16 | N-methyl-N-methylpiperidinium | CH₃SO₄⁻ | –CH₂–(m-C₆H₄)– |
| 17 | N-methyl-N-methylmorpholinium | Cl⁻ | –(CH₂)₃– |
| 18 | N,N-dimethylpyrrolidinium | I⁻ | –(CH₂)₃–CH(CH₃)– |
| 19 | C₂H₅O–C(=O)–CH₂–N⁺(CH₃)₃ | Br⁻ | –(CH₂)₃– |

The following compounds are also prepared analogously to Example 1 and 2:

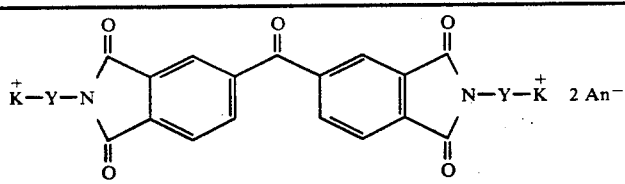

| Example | $\overset{+}{K}-$ | $An^-$ | Y |
|---|---|---|---|
| 20 | CH₃–(CH₂)₁₅–N⁺(CH₃)₂ | Br⁻ | –(CH₂)₃– |
| 21 | CH₃–(CH₂)₁₇–N⁺(CH₃)₂ | Br⁻ | –(CH₂)₃– |

-continued

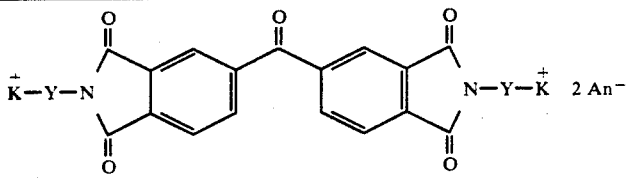

| Example | K— | An⁻ | Y |
|---|---|---|---|
| 22 | benzyl-N⁺(CH₃)₂-CH₃ | Cl⁻ | —CH₂—C(CH₃)(CH₃)—CH₂— |
| 23 | (CH₃)₃N⁺— | CH₃SO₄⁻ | —(CH₂)₃—CH(CH₃)— |
| 24 | (CH₃)₂N⁺-piperazine-N— | " | —(CH₂)₂— |
| 25 | H₂N—CO—CH₂—N⁺(CH₃)₂— | Cl⁻ | —CH₂—C₆H₄— |
| 26 | N-methyl-N-methylpiperidinium | CH₃—C₆H₄—SO₃⁻ | —(CH₂)₃— |
| 27 | CH₃—(CH₂)₁₅—N⁺(CH₃)₂— | phosphotungstomolybdate | —(CH₂)₃— |
| 28 | cyclohexyl-H-N⁺(CH₃)₂ | Br⁻ | " |

Example 29

107.2 g of naphthalene-1,4,5,8-tetracarboxylic dianhydride (0.4 mol) are suspended in 2 l of toluene, 3 g of glacial acetic acid are added and 82.4 g of N,N-dimethyl-1,3-diaminopropane (0.84 mol) are added dropwise with stirring, and the mixture is heated at the boil under reflux and under a water separator for 2 hours. A little undissolved matter is then filtered off under hot conditions, and the filtrate is cooled. The crystalline precipitate is filtered off with suction, washed with toluene and dried in vacuo at 80° C. This gives 145 g (83% of theory) of the compound of the formula

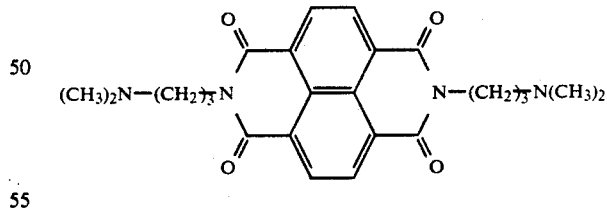

in the form of golden-yellow needles with a metallic lustre of melting point 227° C.

$C_{24}H_{28}N_4O_4$ (436.51), $m/e=436$ ($M^{30}$).

Example 30

43.7 g of the compound of Example 29 (0.1 mol) are suspended in 500 ml of isopropanol, 64 g of 1-bromohexadecane (0.21 mol) are added under $N_2$, and the mixture is heated at the boil under reflux for 20 hours. The crystalline precipitate is filtered off with suction, washed with isopropanol and dried in vacuo at 80° C. This gives 97 g (92.6% of theory) of the compound of the formula

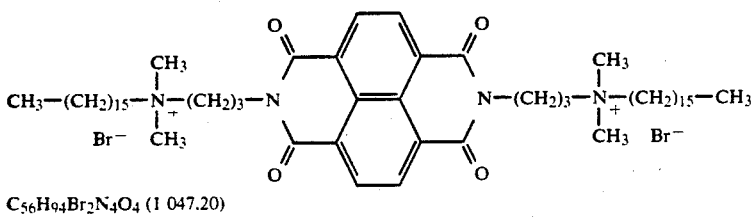

$C_{56}H_{94}Br_2N_4O_4$ (1 047.20)

According to thin layer chromatography the substance is virtually a single substance and it displays fluorescence extinction on the fluorescent silica gel plate. $R_f$ value: 0.31 (mobile phase: 45% by volume of butyl acetate, 33% by volume of glacial acetic acid, 9% by volume of formic acid and 13% by volume of water). It is ground in a jet mill until an average particle size of <10 μ has been reached.

Use 100 g of styrene/n-butyl methacrylate copolymer (molecular weight: 50,000) and 2 g of the compound of Example 30 are mixed at 100° C. in a kneader until homogeneity is reached. After cooling, the resin is pulverized in a jet mill to an average particle fineness of 5 μ. 5 g of this toner powder are charged by rotation with 95 g of a carrier material composed of iron having a polymer coating, and the charge is determined by the blow-off method. It is 25.3 μC/g and is still at an unaltered level after 70,000 copies. The image recordings of copperplate sharpness are superior in sharpness of outline to the charge control substances produced in DE-A 3,604,827, Examples 1 and 34.

The following compounds are prepared analogously to Examples 29 and 30:

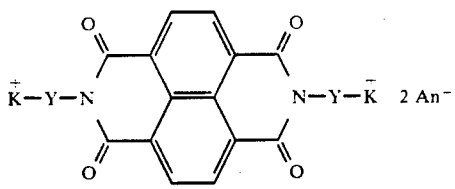

| Example | $\overset{+}{K}$ | $An^-$ | Y |
|---|---|---|---|
| 31 | $CH_3-(CH_2)_{17}-\overset{CH_3}{\underset{CH_3}{\overset{|}{\underset{|}{N{\stackrel{+}{-}}}}}}$ | $Br^-$ | $-(CH_2)_3-$ |
| 32 | $CH_3-(CH_2)_{21}-\overset{CH_3}{\underset{CH_3}{\overset{|}{\underset{|}{N{\stackrel{+}{-}}}}}}$ | $Br^-$ | $-CH_2-CH_2-$ |
| 33 | $CH_3-(CH_2)_{11}-\overset{CH_3}{\underset{CH_3}{\overset{|}{\underset{|}{N{\stackrel{+}{-}}}}}}$ | $CH_3-\text{C}_6\text{H}_4-SO_3^-$ | $-(CH_2)_3-$ |
| 34 | $CH_3-(CH_2)_9-\overset{CH_3}{\underset{CH_3}{\overset{|}{\underset{|}{N{\stackrel{+}{-}}}}}}$ | phosphotungstomolybdate | " |
| 35 | $CH_3(CH_2)_3-\overset{H}{\underset{CH_3}{\overset{|}{\underset{|}{N{\stackrel{+}{-}}}}}}$ | $J^-$ | " |
| 36 | $H_2N-CO-CH_2-\overset{CH_3}{\underset{CH_3}{\overset{|}{\underset{|}{N{\stackrel{+}{-}}}}}}$ | silicomolybdate | $-(CH_2)_2-$ |
| 37 | $C_6H_5-CH_2-\overset{CH_3}{\underset{CH_3}{\overset{|}{\underset{|}{N{\stackrel{+}{-}}}}}}$ | $Cl^-$ | $-(CH_2)_3-$ |
| 38 | $(CH_3)_3\overset{+}{N}-$ | $CH_3SO_4^-$ | " |

-continued

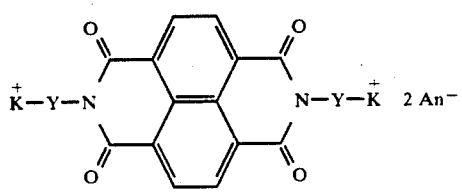

| Example | K⁺ | An⁻ | Y |
|---|---|---|---|
| 39 | (C₂H₅)₃N⁺— | C₂H₅SO₄⁻ | —(CH₂)₂— |
| 40 | H₃C–N⁺(CH₃)(CH₂)₁₅–piperazinyl– | Br⁻ | —CH₂—CH₂— |
| 41 | HOCH₂CH₂–N⁺(CH₃)–piperazinyl– | CH₃—COO⁻ | —CH₂—C(CH₃)₂—CH₂— |
| 42 | cyclohexyl-N⁺(CH₃)₂— | Br⁻ | —(CH₂)₃— |
| 43 | CH₂=CH—CH₂—N⁺(CH₃)₂— | Cl⁻ | —CH₂—(p-C₆H₄)— |
| 44 | 1-methyl-piperidinium-N⁺(CH₃)— | CH₃SO₄⁻ | —CH₂—(m-C₆H₄)— |
| 45 | 4-methyl-morpholinium-N⁺(CH₃)— | Cl⁻ | —(CH₂)₃— |
| 46 | 1-methyl-pyrrolidinium-N⁺(CH₃)— | I⁻ | —(CH₂)₃—CH(CH₃)— |
| 47 | C₂H₅O—C(=O)—CH₂—N⁺(CH₃)₂— | Br⁻ | —(CH₂)₃— |

The compound of the following formula is prepared analogously to Example 30 from the precursor described in DE-A 3,535,496, Example 330:

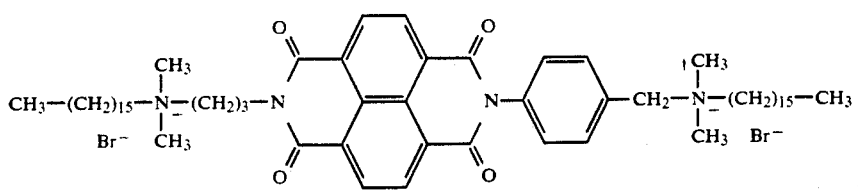

Example 49

296 g of perylenetetracarboxylic dianhydride (0.5 mol) are suspended in 2 l of isopropanol, 4 g of glacial acetic acid are added and 103 g of N,N-dimethyl-1,3- diaminopropane (1 mol) are added dropwise, with stirring, at the boil. The mixture is heated at the boil under reflux for 68 hours. A sample of the suspension dissolves completely in dilute hydrochloric acid. After cooling to room temperature the crystalline precipitate is filtered off with suction, washed with isopropanol and dried in vacuo at 80° C. This gives 273 g of the compound of the formula of glacial acetic acid, 9% by volume of formic acid and 13% by volume of water).

Use

2% by weight of the compound of Example 50, 6% by weight of carbon black and 92% by weight of a styrene/butadiene resin containing 89% by weight of styrene and 11% by weight of butadiene are melted and

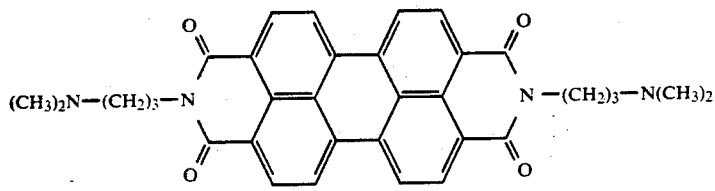

in the form of a dark crystalline powder melting above 300° C. A mass spectrum (DCI excitation) indicates a mass of 561 (M+H)+.
$C_{34}H_{32}N_4O_4$ (560.65).

Example 50

56 g of the compound of Example 49 (0.1 mol) in 500 ml of N-methylpyrrolidone are heated to 100° C. and 64.1 g of 1-bromohexadecane (0.21 mol) are added with stirring and under nitrogen blanketing. The mixture is heated at 120° C. for 48 hours and is then cooled. The crystalline precipitate is filtered off with suction, washed with isopropanol and dried in vacuo at 80° C. This gives 106 g (90% of theory) of the compound of the formula kneaded in an extruder at 100° C. and are then comminuted and ground until the particle diameter is less than 5 μ.

This toner formulation is incorporated in a xerographic image recording system such as is described in U.S. Pat. No. 4,265,990. This is effected by coating a MYLAR ® substrate with a layer of polyvinylcarbazole which produces a charge when exposed to light and into which trigonal selenium has been freely dispersed, and applying on top of this a transparent, charge-transporting layer containing, as the charge-transporting molecules, N,N'-diphenyl-N,N'-bis-(3-methylphenyl)-1,1'-bisphenyl -4,4'-diamine, dispersed in a MAKROLON ® polycarbonate composition.

This gives image recordings of copperplate sharpness

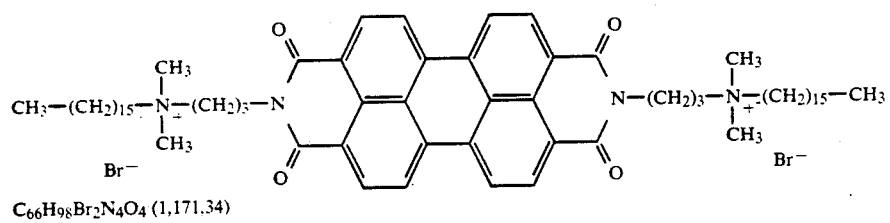

$C_{66}H_{98}Br_2N_4O_4$ (1,171.34)

According to thin layer chromatography the substance is virtually pure and it displays fluorescence extinction on the fluorescent silica gel plate. $R_f$ value: 0.17 (mobile phase: 45% by volume of butyl acetate, 33% by volume which are superior in colour saturation to those prepared in accordance with DE-A 3,604,827, Example 1.

The following compounds are prepared analogously to Examples 49 and 50:

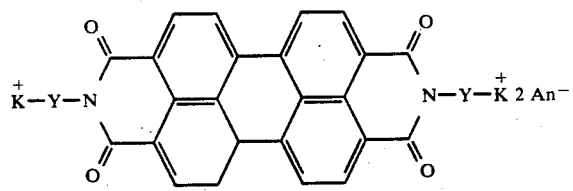

| Example | $\overset{+}{K}-$ | $An^-$ | Y |
|---|---|---|---|
| 51 | $CH_3-(CH_2)_{17}-\overset{\overset{CH_3}{\|}}{\underset{\underset{CH_3}{\|}}{N_+}}-$ | $Br^-$ | $-(CH_2)_3-$ |
| 52 | $CH_3-(CH_2)_{21}-\overset{\overset{CH_3}{\|}}{\underset{\underset{CH_3}{\|}}{N_+}}-$ | $Br^-$ | $-CH_2-CH_2-$ |

-continued

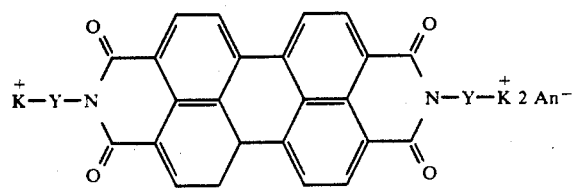

| Example | K⁺— | An⁻ | Y |
|---|---|---|---|
| 53 | CH₃—(CH₂)₁₁—N⁺(CH₃)₂— (with CH₃) | CH₃—C₆H₄—SO₃⁻ | —(CH₂)₃— |
| 54 | CH₃—(CH₂)₉—N⁺(CH₃)₂— | Cl⁻ | " |
| 55 | CH₃(CH₂)₃—N⁺(CH₃)₂— | I⁻ | " |
| 56 | H₂N—CO—CH₂—N⁺(CH₃)₂— | Cl⁻ | —(CH₂)₂— |
| 57 | C₆H₅—CH₂—N⁺(CH₃)₂— | Cl⁻ | —(CH₂)₃— |
| 58 | (CH₃)₃N⁺— | CH₃SO₄⁻ | " |
| 59 | (C₂H₅)₃N⁺— | C₂H₅SO₄⁻ | —(CH₂)₂— |
| 60 | H₃C, CH₃—(CH₂)₁₅— N⁺(piperazine)N— | Br⁻ | —CH₂—CH₂— |
| 61 | HOCH₂CH₂, H₃C— N⁺(piperazine)N— | CH₃—COO⁻ | —CH₂—C(CH₃)₂—CH₂— |
| 62 | cyclohexyl—N⁺(CH₃)₂— (H) | Br⁻ | —(CH₂)₃— |
| 63 | CH₂=CH—CH₂—N⁺(CH₃)₂— | Cl⁻ | —CH₂—C₆H₄— (para) |
| 64 | N-methyl piperidinium (CH₃) | CH₃SO₄⁻ | —CH₂—C₆H₄— (meta) |

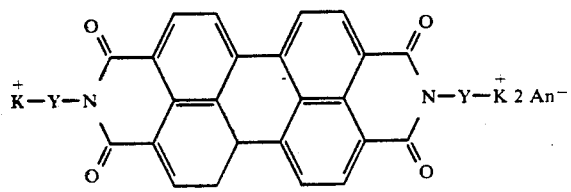

| Example | K— | An⁻ | Y |
|---|---|---|---|
| 65 | morpholine-N⁺(CH₃) | Cl⁻ | —(CH₂)₃— |
| 66 | pyrrolidine-N⁺(CH₃) | J⁻ | —(CH₂)₃—CH(CH₃)— |
| 67 | C₂H₅O—C(=O)—CH₂—N⁺(CH₃)₂— | Br⁻ | —(CH₂)₃— |

Example 68

23,5 g of N,N-dimethyl-1,3-diaminopropane (0.23 mol) are added dropwise, with stirring, to 15.8 g of 3-amino-1-iminoisoindolenine (92% pure, 0.1 mol) in 100 ml of isopropanol at the boil, and the mixture is heated at the boil under reflux for 4 hours, in the course of which $NH_3$ is evolved. After this time a thin layer chromatogram (mobile phase as in Example 2) indicates a complete reaction to give, as a single substance,

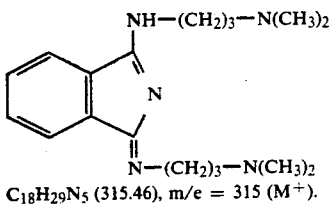

$C_{18}H_{29}N_5$ (315.46), m/e = 315 (M⁺).

This compound is processed further without intermediate isolation to give the compound described in Example 69.

Example 69

The solution of the compound prepared in Example 68 (approximately 0.1 mol) is diluted with 350 ml of isopropanol, 70 g of 1-bromohexadecane (0.23 mol) are added dropwise to the boiling solution under $N_2$ and with stirring, and the mixture is heated to the boil under reflux for 10 hours. After standing for several days at room temperature the colourless, crystalline precipitate is filtered off with suction, stirred with acetone to complete extraction, filtered off with suction, washed with acetone and dried in vacuo at 50° C. This gives 67 g (72.3% of theory) of the compound of the formula

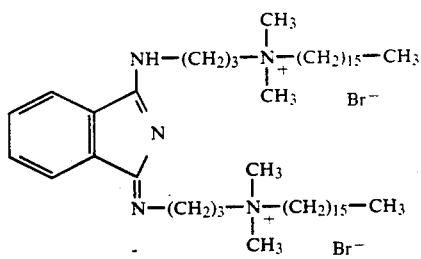

According to thin layer chromatography the substance is virtually pure and it displays fluorescence extinction on the fluorescent silica gel plate.

$R_f$ value: 0.42 (mobile phase as in Example 2).

The compound is ground in a jet mill until an average particle size of <10 µ has been reached.

Use

2% by weight of the compound of Example 69, 6% by weight of carbon black and 92% by weight of a styrene/butadiene resin containing 89% by weight of styrene and 11% by weight of butadiene are melted and kneaded in an extruder at 100° C. and are then comminuted and ground until the particle diameter is less than 5 µ.

This toner formulation is incorporated into xerographic image recording system such as is described in U.S. Pat. No. 4,265,990. This is effected by coating a MYLAR ® substrate with a layer of polyvinylcarbazole which produces a charge when exposed to light and into which trigonal selenium has been freely dispersed, applying on top of this a transparent, charge-transporting layer and applying on top of that a transparent, charge-transporting layer containing, as the charge-transporting molecules, N,N'-diphenyl-N,N'-bis-(3-methylphenyl)-1,1'-bisphenyl 4,4'-diamine, dispersed in a MAKROLON ® polycarbonate composition.

This gives image recordings of copperplate sharpness.

The following compounds are prepared analogously to Examples 68 and 69:

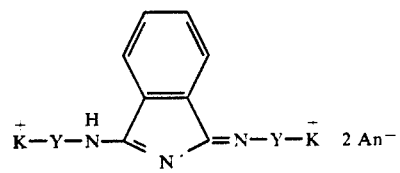

| Example | $\overset{+}{K}-$ | $An^-$ | Y |
|---|---|---|---|
| 70 | $CH_3-(CH_2)_{17}-\overset{CH_3}{\underset{CH_3}{N_+}}-$ | $Br^-$ | $-(CH_2)_3-$ |
| 71 | $CH_3-(CH_2)_{21}-\overset{CH_3}{\underset{CH_3}{N_+}}-$ | $Br^-$ | $-CH_2-CH_2-$ |
| 72 | $CH_3-(CH_2)_{11}-\overset{CH_3}{\underset{CH_3}{N_+}}-$ | $CH_3-\langle\phantom{x}\rangle-SO_3^-$ | $-(CH_2)_3-$ |
| 73 | $CH_3-(CH_2)_9-\overset{CH_3}{\underset{CH_3}{N_+}}-$ | Phosphotungstomolybdate | " |
| 74 | $CH_3-(CH_2)_3-\overset{CH_3}{\underset{CH_3}{N_+}}-$ | $I^-$ | " |
| 75 | $H_2N-CO-CH_2-\overset{CH_3}{\underset{CH_3}{N_+}}-$ | $Cl^-$ | $-(CH_2)_2-$ |
| 76 | $\langle\phantom{x}\rangle-CH_2-\overset{CH_3}{\underset{CH_3}{N_+}}-$ | $Cl^-$ | $-(CH_2)_3-$ |
| 77 | $(CH_3)_3\overset{+}{N}-$ | $CH_3SO_4^-$ | " |
| 78 | $(C_2H_5)_3\overset{+}{N}-$ | $C_2H_5SO_4^-$ | $-(CH_2)_2-$ |
| 79 | $CH_3-(CH_2)_{15}-\overset{H_3C}{\underset{}{N_+}}\langle\phantom{x}\rangle N-$ | $Br^-$ | $-CH_2-CH_2-$ |
| 80 | $HOCH_2CH_2-\overset{}{\underset{H_3C}{N_+}}\langle\phantom{x}\rangle N-$ | $CH_3-COO^-$ | $-CH_2-\overset{CH_3}{\underset{CH_3}{C}}-CH_2-$ |
| 81 | $\langle\phantom{x}\rangle\overset{CH_3}{\underset{CH_3}{N_+}}-$ | $Br^-$ | $-(CH_2)_3-$ |

-continued

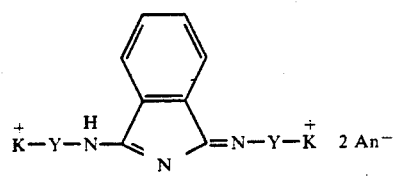

| Example | $\overset{+}{K}-$ | $An^-$ | Y |
|---|---|---|---|
| 82 | $CH_2{=}CH{-}CH_2{-}\overset{CH_3}{\underset{CH_3}{\overset{|}{\underset{|}{N^+}}}}-$ | $Cl^-$ | $-CH_2-C_6H_4-$ (para) |
| 83 | N-methylpiperidinium | $CH_3SO_4^-$ | $-CH_2-C_6H_4-$ (meta) |
| 84 | N-methylmorpholinium | $Cl^-$ | $-(CH_2)_3-$ |
| 85 | N-methylpyrrolidinium | $I^-$ | $-(CH_2)_3-CH(CH_3)-$ |
| 86 | $C_2H_5O-\overset{O}{\overset{\|}{C}}-CH_2-\overset{CH_3}{\underset{CH_3}{\overset{|}{\underset{|}{N^+}}}}-$ | $Br^-$ | $-(CH_2)_3-$ |

We claim:

1. Electrophotographic toners containing resin and pigment particles and an additive which increases the cationic charge as has the general formula $(X^1)^- K^{+1}-Y^1-A-Y^2-K^{+2} (X^2)^-$ wherein
$(X^1)^-$ and $(X^2)^-$ independently of one another are each an anion,
$K^{+1}$ and $K^{+2}$ independently of one another are each selected from the group comprising

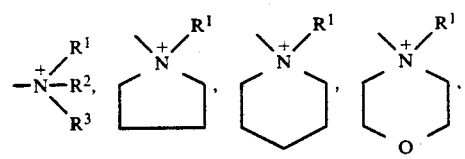

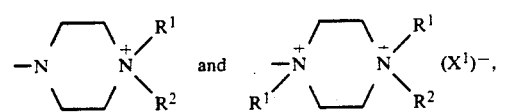 $(X^1)^-$, $R^1$ is selected from the group comprising $C_1-C_{22}$-alkyl, benzyl, phenyl, cyclohexyl and allyl,
$R^2$ is selected from the group comprising hydrogen and $C_1-C_4$-alkyl,
$R^3$ is $C_1-C_4$-alkyl and $Y^1$ and $Y^2$ independently of one another are each $C_2-C_5$-alkylene or $-C_6H_4-CH_2-$ (—m or —p), the bond marked with * being attached to A, and
A is selected from the group comprising tetracarboxylic acid diimides of the formulae

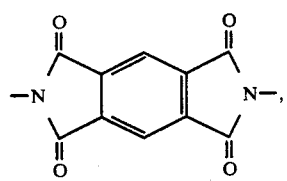

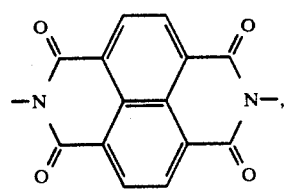

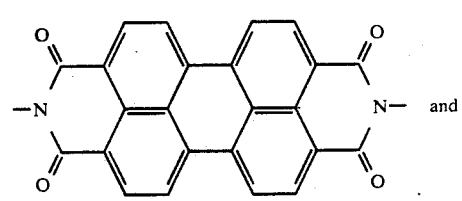 and

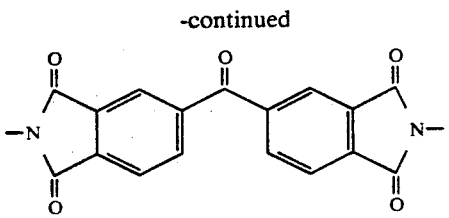

or a 3-amino-1-iminoisoindolenine of the formula

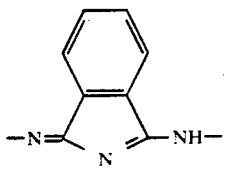

2. Electrophotographic toners according to claim 1, characterized in that

R$^1$ is selected from the group comprising C$_1$-C$_{22}$-alkyl, carbamoyl-C$_1$-C$_2$-alkyl, C$_1$-C$_4$-alkoxy-carbonyl-C$_1$-C$_2$-alkyl, benzyl, cyclohexyl and allyl, R$^2$ and R$^3$ independently of one another are each C$_1$-C$_4$-alkyl and (X$^1$)$^-$, (X$^2$)$^-$, Y$^1$, Y$^2$ and A have the same meaning as in claim 1.

3. Electrophotographic toners according to claim 1, characterized in that

A is an aromatic tetracarboxylic acid diimide of the formula

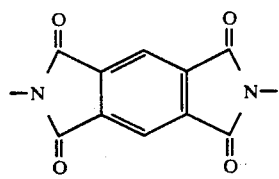

and the remaining symbols have the meaning indicated in claim 1.

4. Electrophotographic toners according to claim 1, characterized in that

A represents an aromatic tetracarboxylic acid diimide of the formula

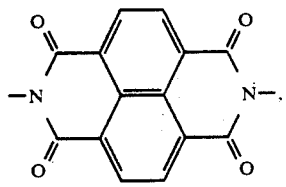

and the remaining symbols have the meaning indicated in claim 1.

5. Electrophotographic toners according to claim 1, characterized in that

A represents an aromatic tetracarboxylic acid diimide of the formula

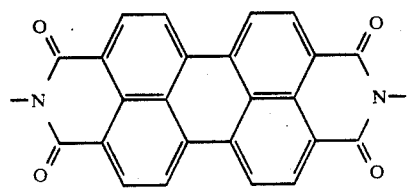

and the remaining symbols have the meaning indicated in claim 1.

6. Electrophotographic toners according to claim 1, characterized in that

A represents an aromatic tetracarboxylic acid diimide of the formula

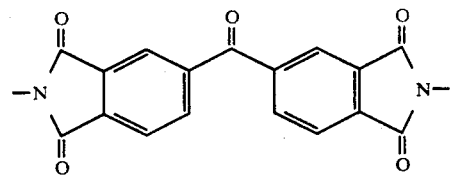

and the remaining symbols have the meaning indicated in claim 1.

7. Electrophotographic toners according to claim 1, characterized in that

A represents an aromatic 3-amino-1-iminoisoindolenine of the formula

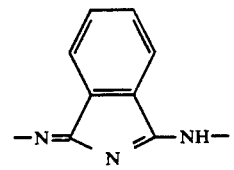

and the remaining symbols have the meaning indicated in claim 1.

8. A method of imaging comprising: (a) forming a latent electrostatic image (b) developing said image with the electrophotographic toner of claim 1.

UNITED STATES PATENT AND TRADEMARK OFFICE
CERTIFICATE OF CORRECTION

PATENT NO. : 5,013,627

DATED : May 7, 1991

INVENTOR(S) : Harnisch et al.

It is certified that error appears in the above-identified patent and that said Letters Patent is hereby corrected as shown below:

Title Page      ABSTRACT: Line 5 delete " $(X^1)^-K^{+1}-Y^1-A-Y^2-K^{+2}(X_2)^-$ " and substitute -- $(X^1)^-K^{+1}-Y^1-A-Y^2-K^{+2}(X^2)^-$ --

Col. 1, line 40      Delete " $-C_6H_4$ " and substitute -- $\pm C_6H_4$ --

Col. 25, line 42      Delete " $(X^1)^-K^{+1}-Y^1-A-Y^2-K^{+2}(X^2)^{31}$ " and substitute -- $(X^1)^-K^{+1}-Y^1-A-Y^2-K^{+2}(X^2)^-$ --

Col. 26, line 39      Delete " $-C_6H_4$ " and substitute -- $\pm C_6H_4$ --

Signed and Sealed this

Twenty-third Day of February, 1993

*Attest:*

STEPHEN G. KUNIN

*Attesting Officer*      *Acting Commissioner of Patents and Trademarks*